United States Patent [19]
Park et al.

[11] Patent Number: 5,958,742
[45] Date of Patent: Sep. 28, 1999

[54] **MICROBIOLOGICAL METHOD FOR PREPARING SPHINGOLIPIDS USING A NOVEL YEAST *PICHIA CIFERRII* DSCC 7-25**

[75] Inventors: Chang Seo Park, Kwacheon; Ji Hean Jeong, Suwon; Sung Yong Hong, Seoul; Woo Seok Choi, Gunpo, all of Rep. of Korea

[73] Assignee: Doosan Corporation, Seoul, Rep. of Korea

[21] Appl. No.: 09/119,958

[22] Filed: Jul. 21, 1998

[51] Int. Cl.$^6$ .............................. C12P 13/00; C12P 13/02; C12N 1/14
[52] U.S. Cl. ..................... 435/128; 435/129; 435/254.23; 435/938
[58] Field of Search ...................... 435/128, 129

[56] References Cited

FOREIGN PATENT DOCUMENTS 0 688 871 A2  12/1995  European Pat. Off. .
WO 94/10131  5/1994  WIPO .

OTHER PUBLICATIONS

Stodola et al., J. of Bio. Chem., 235:9, Sep. 1960, pp. 2584–2585.

Barenholz et al., Biochim. Biophys. Acta, 248 (1971) pp. 458–465.

Zhao et al., J. of Bio. Chem., 269:34, Aug. 26, 1994, pp. 21480–21488.

*Primary Examiner*—Herbert J. Lilling
*Attorney, Agent, or Firm*—Kenyon & Kenyon

[57] ABSTRACT

The present invention relates to a microbiological process for preparing sphingolipids, especially, tetraacetylphytosphingosine(TAPS), using novel yeast cell *Pichia ciferrii* DSCC 7-25 under optimal fermentation conditions. Further, this invention concerns a novel yeast cell *Pichia ciferrii* DSCC 7-25 and it's isolation method from wild type of *Pichia ciferrii* strain.

3 Claims, 1 Drawing Sheet

MICROBIOLOGICAL METHOD FOR PREPARING SPHINGOLIPIDS USING A NOVEL YEAST PICHIA CIFERRII DSCC 7-25

BACKGROUND OF THE INVENTION

1. Field of the Invention

The present invention relates to a microbiological process for preparing sphingolipids, especially, tetraacetylphytosphingosine(TAPS), using a novel yeast *Pichia ciferrii* DSCC 7-25 under defined fermentation conditions. Further, this invention concerns a novel yeast *Pichia ciferrii* DSCC 7-25 and it's isolation method from the parental *Pichia ciferrii* strain ATCC 14091.

2. Description of Prior Art

The term "sphingolipids" refers to a group of lipids derived from sphingosine. Further, sphingolipids contain sphingosine, dihydrosphingosine or phytosphingosine as a base in amide linkage with a fatty acid. Sphingosine or phytosphingosine bases may be used as starting materials in the synthesis of a particular group of sphingolipids, namely ceramides. Ceramides are main lipid component of the stratum corneum, which has an important barrier function. Therefore, the skin cosmetic products having ceramides has a function for moisture-retaining properties of the skin.

Currently, heterogenous sphingolipid preparations for cosmetics are mainly extracted from animal sources. Obviously, this is a rather costly process on an industrial scale. Moreover, it has been found that these materials are potentially unsafe due, for example, to the possible presence of bovine spongiform encephalomyelitis (BSE) in bovine tissue. Thus, the cosmetic industry has demonstrated an increasing interest in new sources of pure, well-defined sphingolipids, which are obtained from sources other than animal tissues.

Microorganisms such as the yeasts *Pichia ciferrii*, formerly indicated as *Hansenula ciferrii* and *Endomycopsis ciferrii* (Stodola and Wickerham, 1960; Wickerham and Stodola, 1960; Wickerham et al., 1954; Wickerham, 1951) have been found to produce sphingolipids as such, as well as sphingosine, phytosphingosine and/or derivatives thereof. This discovery provides sources for sphingolipids themselves and for starting materials for the production of other commercially valuable compounds which could offer a valuable alternative to the use of animal sources of these compounds.

The biosynthetic pathway of tetraacetylphytosphingosine (TAPS) in *Pichia ciferrii* was described by Barenholz et al (1973). The biosynthetic pathway for sphingosine and dihydrosphingosine is proposed by Dimari et al. (1971). Barenholz et al. (1971 & 1973) investigated the metabolic background of the production of TAPS and other sphingolipid bases in four strains of *Pichia ciferrii*. In the later study, the profiles of four microsomal enzymes specific for the biosynthesis of acetylated sphingosine bases of a low (*Pichia ciferrii* NRRL Y-1031, E-11, sex b, 8-20-57) and a high producer (*Pichia ciferrii* NRRL Y-1031, F-60-10) were compared. It was found that the specific activity of 3-keto dihydrosphingosine synthetase and the long-chain base acetyl-CoA acetyltransferase were increased 5–10 fold and 30 fold respectively, as compared with the low producer, whereas the activities of palmityl thiokinase and 3-ketodihydrosphingosine reductase were similar. This indicates that in the low producer, the activity of the 3-ketodihydrophingosine synthetase and the long-chain base acetyl-CoA acetyltransferase is the limiting steps in the synthesis of acetylated sphingosines. Under the defined growth conditions, *Pichia ciferrii* NRRL Y-1031 F-60-10 was found to produce 300 $\mu$moles/L sphingosine (about 0.15 g/L) bases, of which, at least 250 $\mu$moles/L were extracellular. Even where culture conditions were optimized for TAPS production, only 0.485 g/L TAPS (0.024 g TAPS/g dry yeast) was obtained (Maister et al., 1962).

Maister, using the F-60-10 mating type strain, was able to produce up to 300 mg/L in a pilot scale batch mode fermentation using glucose as a carbon source at 25° C. The TAPS produced is the D-D-erythroisomer, which has the same stereochemistry as the phytosphingosine occurring in the human skin. TAPS may be easily deacetylated to phytosphingosine. However, the yields of TAPS are too low to be of any practical value for commercial production.

Recently, many researchers have been attempted to improve the productivity of sphingolipids using mutant cells of *Pichia ciferrii*. According to the disclosure in WO 94/10131 (PCT/GB93/02230) maximum 2700 mg/L of TAPS production was reported using *Pichia ciferrii* NRRL Y-1031 F-60-10 in fed batch mode fermentation with 22.5 mg/L/h of TAPS productivity. Further, in WO 95/12683 (PCT/EP 94/03652), mutants derived from the mating type strain of *Pichia ciferrii* F-60-10 showed 40~60% increased TAPS productivity compared to the parental strain. On the other hand, EP 0 688 871 A2 disclosed the selection and isolation of novel mutant of *Pichia ciferrii* F-60–10. Using this mutant, average 500~1,000 mg/L and maximum 5,000 mg/L of TAPS production was reported, even though the productivity of TAPS is only 30~42 mg/L/h.

However, any of the yeast strains studied to date, even *Pichia ciferrii* NRRL Y-1031 F-60-10, does not produce sufficient amounts of sphingolipid bases such as sphingosine, phytosphingosine or derivatives thereof to be an efficient, economically attractive source of such compounds.

In the early studies of Wickerham and his colleagues (Wickerham and Stodola, 1960), the production of sphingolipids, specifically TAPS was observed to be related to sexuality of the *Pichia ciferrii* strains. A high TAPS producer mating type NRRL Y-1031, F-60-10 was the one of the mating type isolate derived from the parental strain NRRL Y-1031(ATTC 14091), which was diploid. They also reported that a mating type of one sex(a) had a tentency of producing much higher level of TAPS than the other sex(b). It appeared, however, that there were some other genetic factor(s) affecting production of sphingolipids than sexuality. The strain Y-1031 mating type 11 produced much less TAPS than the strain Y-1031 mating type F-60-10 eventhough it had same sex type with the mating type F-60-10.

Based on the previous findings described above, we reasoned that genetic recombinations during meiosis of a diploid *Pichia ciferrii*, which results in formation of haploid spores, could give rise to a novel haploid mating type *Pichia ciferrii* strain with higher TAPS production yield than mating type F-60-10. In addtion, we employed a selection scheme that favors isolation of high producer of TAPS out of the spore pools. Calcium ion has been shown to affect the biosynthesis of sphingolipids by modulating activities of key enzymes involved in the pathway. Depletion of calcium ions by addition of EGTA that chelates calcium ions in the selection medium prevents the yeast cells to grow probably because it prvents synthesis of sphingolipids in the cell. Therefore, new haploid isolates that can grow in those selection environment are likely high producers of TAPS.

SUMMARY OF THE INVENTION

The object of the present invention is to provide novel yeast isolates of *Pichia ciferrii*, which were deposited to Korean Culture Center of Microorganism, Department of Food Engineering, College of Eng., Yonsei University, Sodaemungu, Seoul 120–749 Korea with accession number KCCM-10131 on Jun. 30, 1998 under Budapest treaty, for preparing tetraacetylphytosphingosine (TAPS) with high productivity.

Another object of the present invention is to provide a process for maximum production of TAPS using a novel isolate, *Pichia ciferrii* DSCC 7-25 (KCCM-10131) comprising the steps of:

i) a fermentation with the yeast strain until maximum concentration of TAPS in fermentation medium becomes 5~15 g/L wherein
   a) composition of YMgl medium comprises yeast extract, malt extract, peptone, glycerol containing $CaCl_2$ and citrate
   b) temperature of cultivation is 22~28° C.;
   c) agitation speed of the medium is 400~600 rpm;

ii) transfering the fermentation mass to aging tank;

iii) separating the TAPS using organic solvent; and iv) purifying the TAPS by silica gel column chromatography.

The other object of the present invention is to provide the process for maximum production of TAPS using a new *Pichia ciferrii* strain DSCC 7-25 (KCCM-10131) characterized in the fermentation is a batch fermentation, and the composition of YMgl medium comprises 0.2~0.4 (w/v)% of yeast extract, 0.2~0.4 (w/v)% of malt extract, 0.3~0.7 (w/v)% of peptone, 8.0~12.0 (w/v)% of glycerol containing 5~15 mmole of $CaCl_2$ and 0.4~0.7 (w/v)% of citrate.

The further object of the present invention is to provide the process for maximum production of TAPS using a new *Pichia ciferrii* strain DSCC 7-25 (KCCM-10131) characterized in the fermentation is a fed batch fermentation, and the composition of YMgl medium comprises 0.3~0.5 (w/v)% of yeast extract, 0.3~0.5 (w/v)% of malt extract, 0.3~0.7 (w/v)% of peptone, 15.0~18.0 (w/v)% of glycerol containing 10~20 mmole of $CaCl_2$ and 0.5~0.9 (w/v)% of citrate.

DETAILED DESCRIPTION OF THE INVENTION

Figure 1:
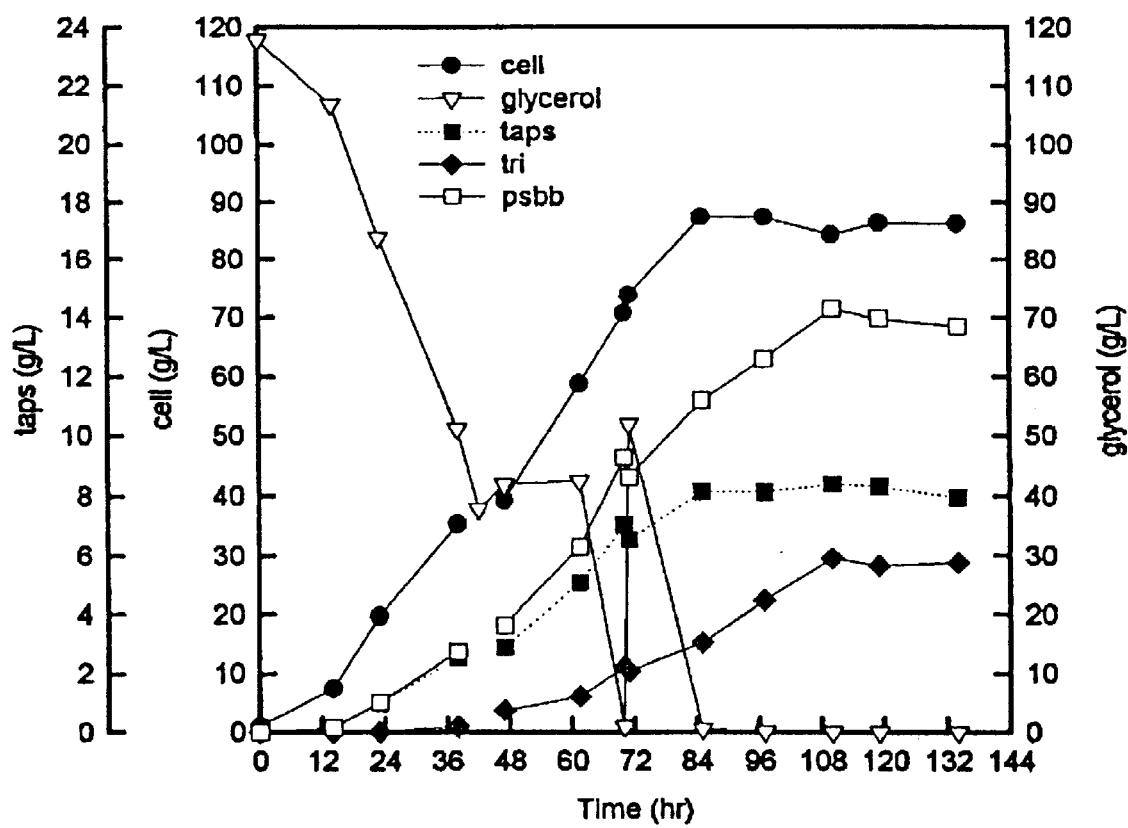
FIG. 1 shows the TAPS production in a fed batch fermentation using DSCC 7-25.

The novel *Pichia ciferrii* DSCC 7-25 strain used in the present invention are isolated by following methods, in which any mutagenesis steps are not involved.

The parental diploid yeast *Pichia ciferrii* ATCC-14091 is cultivated in the YMgl medium [0.2~04 (w/v)% of yeast extract, 0.2~0.4 (w/v)% of malt extract, 0.3~0.7 (w/v)% of peptone, 2.5~3.5 (w/v)% of glycerol] with agitation, and is spread in the spore formation medium [3~7% of malt extract and 4~5% of agar]. Then, hat-shape spores are obtained, and single spores are selected by heat shock and cell wall degrading enzymes such as glusulase or Zymolyase that hydrolyze the cell wall of vegitative cells but not that of spores. This treatment efficiently enriches spores from the sporulated cell cultures, especially from the poorly sporulated cell cultures. For the selection of obtained single spore yeast derivatives, the selected cells are cultivated in YMgl plate medium [0.2~0.4 (w/v)% of yeast extract, 0.2~0.4 (w/v)% of malt extract, 0.3~0.7 (w/v)% of peptone, 2.5~3.5 (w/v)% of glycerol and 2~30 mmole of EGTA], then cells are selected according to the amount of the release of sphingolipids. Finally, *Pichia ciferrii* DSCC 7-25 is isolated as the most sphingolipids release cell compared to those of other cells by the TLC and HPLC analysis. These isolates were deposited to Korean Culture Center of Microorganism with accession number KCCM-10131.

Followings are fermentation methods for producing TAPS using the selected yeast *Pichia ciferrii* DSCC 7-25.

The selected yeast *Pichia ciferrii* DSCC 7-25 are seed cultured in the cultivation medium, and concentrated cells are obtained. The seed cells are cultivated in YMgl medium with the yeast strain until maximum concentration of TAPS in fermentation medium becomes 5~7 g/L. Further, the composition of YMgl medium comprises 0.2~0.4 (w/v)% of yeast extract, 0.2~0.4 (w/v)% of malt extract, 0.3~0.7 (w/v)% of peptone, 8.0~12 (w/v)% of glycerol containing 5~15 mmole of $CaCl_{2\ 0.4~0.7}$ (w/v)% of serine and 0.4~0.7 (w/v)% of citrate.

The formation of sphingolipids is controlled by the concentration of calcium cation ($Ca^{++}$), because the activity of serine-palmitoyl transferase (SPT) is enhanced by the addition of calcium cation in the medium. However, in the case of *Pichia ciferrii* NRRL Y-1031, the production of sphingolipids decreases in addition to the calcium cation in the medium.

On the other hand, the addition of serine in the medium increases the production of TAPS, since sphingolipids are biosynthesized by the reaction between serine and palmitoyl-CoA. Therefore, serine is also a limiting factor of biosynthesis of sphingolipids. According to the addition of calcium cation and serine in the fermentation medium, the productivity of TAPS has been increased up to 4~5 fold in comparison to the productivity without adding such compounds in the medium.

The fermentation conditions are optimal, when the temperature of cultivation is 22~28° C. and agitation speed of the medium is 400~600 rpm. After the fermentation, the biomass including sphingolipids is transferred to aging tank. Then, the fermented biomass is aged for 2 days at 3~5° C. The cells are precipitated and removed in the bottom of tank, and the sphingolipids are extracted by organic solvent. Finally, over 95% purified TAPS is obtained by the silica gel column chromatography.

The obtained TAPS can be converted to sphingosine or phytosphingosine by deacetylation in the basic solution, such as, KOH or NaOH. Using this sphingosine or phytosphingosine, the ceramide and it's derivatives can be obtained by N-acylation reaction with fatty acid. The fatty acid used for this reaction is any of saturated or unsaturated fatty acid having 6~40 of carbon atoms and 0~3 of double bonds. Further, this reaction is carried out by enzyme reaction or chemical reaction. In case of chemical reaction, carbodiimide, carbodiimidazole, 1,2-dihydroquinolon and/or hydroxybenzotriazole can be used as binding reagent.

The present invention can be explained more specifically by following examples. However, the scope of the present invention cannot be limited to following examples.

EXAMPLE 1

Isolation of *Pichia ciferrii* DSCC 7-25

A diploid *Pichia ciferrii* ATCC-14091 is cultivated in the YMgl medium [0.2~0.4 (w/v)% of yeast extract, 0.2~0.4 (w/v)% of malt extract, 0.3~0.7 (w/v)% of peptone, 2.5~3.5 (w/v)% of glycerol] with agitation at 25° C. for three days. Then, the obtained cells are spread and cultivated in 0.1~0.5 ml of the spore formation medium [3~7% of malt extract and 4~5% of agar] in room temperature for 7~10 days. Then, hat-shape spores are obtained. The efficiency of spore formation is 6~8%. Obtained spores are enriched by a combination of heat treatment and Zymolyase treatment for selection. The heat treatment is carried out to the 1~2 ml of spore suspension (6~10×10$^7$ cells/ml) at 55° C. for 1~5 minutes and followed by treatment of Zymolyase 60,000 (10 mg/ml) for 0.5 to 2 hours at 30° C. First selection is carried out to isolate colonies different from the parental cells in shape, color and size. 50 colonies are selected among 400 colonies grown from the enriched spore pool.

For the second selection of obtained single spore yeast derivatives, the r selected cells are cultivated in YMgl plate medium [0.2~0.4 (w/v)% of yeast extract, 0.2~0.4 (w/v)% of malt extract, 0.3~0.7 (w/v)% of peptone, 2.5~3.5 (w/v)% of glycerol and 2 30 mmole of EGTA] at 25° C. for 4 days. Then, cells are selected according to the amount of the release of sphingolipids. Following table shows the produced TAPS amount of secondary selected strains.

TABLE 1

The produced amount of TAPS of haploid isolates in YMgl medium

| Strain | Produced amount of TAPS(mg/L) |
|---|---|
| 14091 | 120 |
| 2-28 | 94 |
| 7-24 | 93 |
| 7-25 | 319 |
| 7-28 | 199 |
| 7-29 | 184 |
| 7-40 | 116 |
| 7-44 | 83 |
| F-60-10 | 241 |

Finally, *Pichia ciferrii* DSCC 7-25 which is isolated as the most sphingolipids release cell compared to those of other cells by the TLC and HPLC analysis. The production yield of TAPS by *Pichia ciferrii* DSCC 7-25 is even 30% higher than that of F-60-10 strain which is known as the best strain for producing TAPS.

EXAMPLE 2

Comparision with *Pichia ciferrii* DSCC 7-25 and *Pichia ciferrii* F-60-10

The productivity of TAPS in the present invention is measured in comparison with that of *Pichia ciferrii* DSCC 7-25. Following is the comparison data between *Pichia ciferrii* DSCC 7-25 and *Pichia ciferrii* F-60-10.

TABLE 2

Comparision data between *Pichia ciferrii* DSCC 7-25 and *Pichia ciferrii* F-60-10

|  | DSCC 7-25 | F-60-10 |
|---|---|---|
| Doubling time (hour) | 1.5 | 3.0 |
| Concentration of biomass (g/L) | 29.7 | 15 |
| TAPS Titre (mg/L) | 319[a] | 241[b] |
| Specific yield of TAPS (mg/gdw) | 10.7 | 16.1 |
| Volumetric productivity (mg TAPS/L/H) | 4.6 | 1.7 |

※ Fermentation condition: YMgl medium (3% of glycerol), 25° C., 250 rpm

TABLE 2-continued

Comparision data between *Pichia ciferrii* DSCC 7-25 and *Pichia ciferrii* F-60-10

|  | DSCC 7-25 | F-60-10 |
|---|---|---|

[a]: hours to the end of fermentation was 70 hours
[b]: hours to the end of fermentation was 144 hours As shown in the table, the strain DSCC 7-25 has much better volumetric productivity, by which the cost of production is determined.

EXAMPLE 3

Optimization of fermentation condition for *Pichia ciferrii* DSCC 7-25—synergistic effect of CaCl$_2$ and serine on the production of TAPS The selected haploid strain *Pichia ciferrii* DSCC 7-25 are pr-cultured in the cultivation medium, and concentrated cells are obtained. The obtained cells are cultivated in YMgl medium at 30°C., in 250 rpm for 3 days. The composition of YMgl medium comprises 0.2~0.4 (w/v)% of yeast extract, 0.2~0.4 (w/v)% of malt extract, 0.3~0.7 (w/v)% of peptone, 2.5~3.5 (w/v)% of glycerol containing 10 mmole of CaCl$_2$ and 0.5 (w/v)% of serine.

The formation of sphingolipids is controlled by the concentration of calcium cation (Ca$^{++}$), because the activity of serine-palmitoyl transferase (SPT) is enhanced by the addition of calcium cation in the medium. However, in case of *Pichia ciferrii* NRRL Y-1031 mating type F-60-10, the production of sphingolipids decreases by addition of calcium cation in the medium. Following table shows the effect of calcium ion on the TAPS production between *Pichia ciferrii* DSCC 7-25 and *Pichia ciferrii* F-60-10.

TABLE 3

Calcium cation effect to TAPS production

| | TAPS production (mg/L) | | |
|---|---|---|---|
| Strain | w/o CaCl$_2$ | CaCl$_2$ (10 mM) | Effect |
| DSCC 7-25 | 396 | 744 | +1.9 |
| F-60-10 | 241 | 43 | −5.6 |

On the other hand, the addition of serine in the medium increases the production of TAPS, since sphingolipids are biosynthesized by the reaction between serine and palmitoyl-CoA. Following table shows the effect to TAPS productivity of calcium cation and serine to *Pichia ciferrii* DSCC 7-25.

TABLE 4

| | Production yield of TAPS | | |
|---|---|---|---|
| Medium | Production yield of TAPS | | |
| YMgl + | mg/L | mg/gdw | mg/L/H |
| None | 284 | 22.3 | 3.94 |
| * CaCl$_2$ | 816 | 58.3 | 11.33 |
| ** Serine | 784 | 54.8 | 10.88 |
| CaCl$_2$ + Serine | 1,065 | 88.2 | 14.79 |

* CaCl$_2$ 10 mM,
** Serine 5 g/L

EXAMPLE 4

Optimization of fermentation conditions for *Pichia ciferrii* DSCC 7-25: batch and fed batch mode of fermentations for pilot scale The fermentation conditions are further optimized in order to obtain maximum yield of TAPS production in a 500 L pilot scale fermentation. Optimized conditions include the temperature of cultivation is 22~28° C. and agitation speed of the medium is 200~250 rpm. In addition, other physiological factors affecting the production of TAPS as well as lipid biosynthesis are searched and the optimal concentrations and conditions for each element are determined. Those elements include pH, concentration of magnesium and calcium ion, organic acids such as citrate.

TABLE 5

Production yield of TAPS at a optimized condition

| Strain | *Pichia ciferrii* DSCC 7-25 | |
|---|---|---|
| Mode of Fermentation | Batch(1) | Fed batch(2) |
| Doubling Time (hour) | 1.5 | 1.5 |
| Concentration of biomass (g/L) | 41.6 | 85 |
| TAPS titre (mg/L) | 6206 | 14000 |
| Specific yield of TAPS (mg/L) | 149.2 | 164.7 |
| Volumetric productivity (mg TAPS/L/H) | 51.7 | 129.6 |

✕ Fermentation conditions: Temp, 25° C., Agitation, 210 rpm, Aeration, 0.2 vvm and the initial pH 7.5.
(1): hours to the end of fermentation was 120 hours
(2): hours to the end of fermentation was 108 hours Since the production of TAPS by the yeast *Pichia ciferrii* is growth associated, supplement of a portion of the nutrients including glycerol has been shown to result in accumulation of TAPS and its derivatives in the culture until the nutrients are depleted. Using a fed-batch mode of fermentation, in which glycerol was added stepwisely to the fermentation broth up to 180 grams/L, the resulted production yield of TAPS and its derivatives reached to 14 grams/L as shown in the Table 5 and FIG. 1.

After the fermentation, the biomass including sphingolipids is transferred to aging tank. Then, the fermented biomass is aged for 2 days at 3~5° C. The cells are precipitated and removed in the bottom of tank, and the sphingolipids are extracted by a process that is basically same as a process published by Wickerham et al. (1962) . Finally, over 95% purified TAPS is obtained by the silica gel column chromatography.

We claim:

1. A process for maximum production of TAPS using a new *Pichia ciferrii* strain DSCC 7-25 (KCCM-10131) comprising the steps of:

i) a fermentation with the yeast strain until maximum concentration of TAPS in fermentation medium becomes 5~15 g/L wherein
      a) composition of YMgl medium comprises yeast extract, malt extract, peptone, glycerol containing $CaCl_2$ and citrate;
      b) temperature of cultivation is 22~28° C.;
      c) agitation speed of the medium is 400~600 rpm;

ii) transfering the fermentation mass to aging tank;

iii) separating the TAPS using organic solvent; and iv) purifying the TAPS by silica gel column chromatography.

2. The process for maximum production of TAPS using a new *Pichia ciferrii* strain DSCC 7-25 (KCCM-10131) according to claim 1, wherein fermentation is a batch fermentation, and the composition of YMgl medium comprises 0.2~0.4 (w/v)% of yeast extract, 0.2~0.4 (w/v)% of malt extract, 0.3~0.7 (w/v)% of peptone, 8.0~12.0 (w/v)% of glycerol containing 5~15 mmole of $CaCl_2$ and 0.4~0.7 (w/v)% of citrate.

3. The process for maximum production of TAPS using a new *Pichia ciferrii* strain DSCC 7-25 (KCCM-10131) according to claim 1, wherein fermentation is a fed batch fermentation, and the composition of YMgl medium comprises 0.3~0.5 (w/v)% of yeast extract, 0.3~0.5 (w/v)% of malt extract, 0.3~0.7 (w/v)% of peptone, 15.0~18.0 (w/v)% of glycerol containing 10~20 mmole of $CaCl_2$ and 0.5~0.9 (w/v)% of citrate.

* * * * *